United States Patent
Linders et al.

(10) Patent No.: US 7,435,817 B2
(45) Date of Patent: Oct. 14, 2008

(54) C-14 OXIDATION OF MORPHINE DERIVATIVES

(75) Inventors: Joannes Theodorus Maria Linders, Eindhoven (NL); Pieter Vrijhof, Diosynth (NL)

(73) Assignee: N.V. Organon (NL)

( * ) Notice: Subject to any disclaimer, the term of this patent is extended or adjusted under 35 U.S.C. 154(b) by 306 days.

(21) Appl. No.: 10/487,884

(22) PCT Filed: Aug. 15, 2002

(86) PCT No.: PCT/EP02/09280

§ 371 (c)(1),
(2), (4) Date: Sep. 24, 2004

(87) PCT Pub. No.: WO03/018588

PCT Pub. Date: Mar. 6, 2003

(65) Prior Publication Data

US 2005/0038250 A1    Feb. 17, 2005

(30) Foreign Application Priority Data

Aug. 23, 2001    (EP) .................................. 01203187

(51) Int. Cl.
*C07D 489/02* (2006.01)
*C07D 489/08* (2006.01)
*C07D 491/08* (2006.01)

(52) U.S. Cl. .............................. 546/44; 546/45; 546/46

(58) Field of Classification Search .................. 546/45, 546/46, 44
See application file for complete search history.

(56) References Cited

U.S. PATENT DOCUMENTS

| | | | |
|---|---|---|---|
| 5,112,975 A * | 5/1992 | Wallace ........................ | 546/45 |
| 5,869,669 A * | 2/1999 | Huang et al. .................. | 546/45 |
| 5,922,876 A * | 7/1999 | Huang et al. .................. | 546/45 |
| 6,008,355 A * | 12/1999 | Huang et al. .................. | 546/45 |

FOREIGN PATENT DOCUMENTS

| EP | 158476 | 10/1985 |
|---|---|---|
| WO | 00 66588 | 11/2000 |

OTHER PUBLICATIONS

Neumeyer et al, Biomed. & Enviro. Mass Spec., 13(5) pp. 223-229 (1986).*

Abdel-Maksoud et al., "GC/MS Characterization of the Products from the Stereo-And Regioselective O-Demethylation of Dimethoxyaporphines with *Cunninghamella elegans*," *New Trends in Natural Products Chemistry 1986:* Eds. Atta-ur-Rahman et al., *Studies in Organic Chemistry 26* (1986) 357-370.

* cited by examiner

*Primary Examiner*—Janet L. Andres
*Assistant Examiner*—Raymond Covington
(74) *Attorney, Agent, or Firm*—Susan Hess

(57) ABSTRACT

The present invention relates to process for the preparation of a 14-hydroxynormorphinone derivative of formula IV

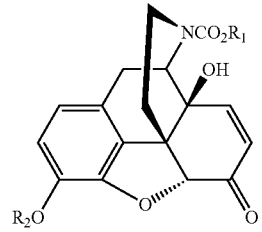

IV comprising reacting the compound of formula III,

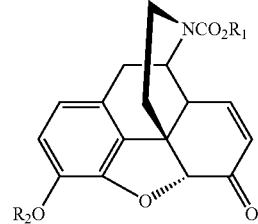

III with a cobalt (II) oxidant in the presence of a mild base and air or oxygen as the cooxidant;
wherein $R_1$ is (1C-7C)alkyl optionally substituted with one or more chlorines, butenyl, vinyl, benzyl, phenyl or naphthyl; and
$R_2$ is benzyl or benzyl substituted with one or more (1C-6C) alkoxy group or benzyl substituted with one or more halogen.

The process is very suitable in the production of noroxymorphone.

22 Claims, No Drawings

C-14 OXIDATION OF MORPHINE DERIVATIVES

The invention relates to a process for the production of 14-hydroxynormorphinone derivatives, to a new synthetic route for producing noroxymorphone, as well as to new intermediates in said route.

Noroxymorphone is a key intermediate for the production of important medicinal opioids, such as naltrexone and naloxone. The common starting material for the production of these opioids is thebaine from which they are readily synthesized. However, thebaine has only a low natural abundance in poppy heads and opium. As the supply of thebaine is limited and the demand is increasing, many alternative approaches have been made for the preparation of 14-hydroxymorphine derivatives. See for example EP 0,158,476, U.S. Pat. No. 5,922,876, and the references cited therein.

Further, in an attempt to remove the requirement for (the preparation of) thebaine, Coop et al. (Tetrahedron 55 (1999), 11429-11436; WO 00/66588) recently described an oxidative method for the production of 14-hydroxycodeinone in a yield of 51% from codeinone, using $Co(OAc)_3$ as the metallic oxidant in acetic acid at room temperature. Other oxidative conditions with metallic oxidants, such as $Co(OAc)_3$ under other conditions, $FeCl_3$, $Co(OAc)_2$ in combination with several cooxidants, $RuO_4$, $Mn(OAc)_3$, $Cu(OAc)_2$, and others, proved to be not very useful according to Coop.

Surprisingly, and in spite of the findings of Coop, it has now been found that in the production of 14-hydroxynormorphinone derivatives of formula IV from compounds of formula III cobalt (II) salts can be used as efficient oxidants when the reaction is performed in the presence of a mild base and oxygen or air is used as cooxidant. Therefore, the invention relates to a process for the preparation of a 14-hydroxynormorphinone derivative of formula IV

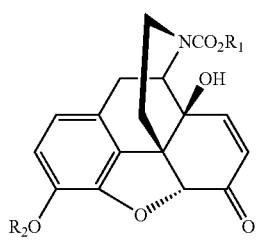

IV comprising reacting the compound of formula III,

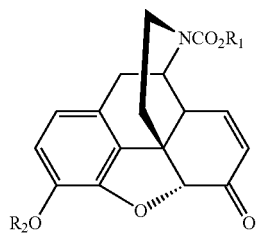

III with a cobalt (II) oxidant in the presence of a mild base and air or oxygen as the cooxidant; wherein $R_1$ is (1-7C)alkyl optionally substituted with one or more chlorines (such as 1,1,1-trichloroethyl), butenyl, vinyl, benzyl, phenyl or naphthyl; and $R_2$ is benzyl or benzyl substituted with one or more (1-6C)alkoxy group or benzyl substituted with one or more halogen.

The oxidation process of the present invention is an efficient process with good yields, which are significantly improved when compared to the process described by Coop et al.

The cobalt (II) oxidant according to the present invention may be selected from a range of cobalt (II) salts, such as $CoF_2$, $CoCl_2$, $CoBr_2$, Co(II)sulfate, Co(II)nitrate, Co(II)acetate, Co(II)propionate, and the like, and mixtures thereof. The preferred oxidant in the process of this invention is $Co(OAc)_2$ and the preferred cooxidant is air. The reaction mixture of this oxidation process is a heterogeneous system; the oxidant dissolves only in minor amounts in the organic solvent that is used. The amount of cobalt (II) salts used is not very critical, as long as the system is heterogeneous, and a skilled person will know to choose sufficient amounts thereof. The cooxidant is introduced into the reaction mixture by bubbling it through the solution, while stirring.

A person skilled in the art is aware what type of base are meant with the term mild bases, however preferred bases are sodium acetate, potassium acetate, sodium phosphate and potassium phosphate. Most preferred is sodium acetate.

Preferably $R_1$ is (1-7C)alkyl, and most preferred is ethyl. For $R_2$ benzyl is most preferred. The oxidation process according to the present invention is performed in an organic solvent well-suited for dissolution of this type of compounds, preferably (1-4C)alcohols or mixtures thereof. Preferred is ethanol.

The reaction temperature is usually higher than room temperature, and may be chosen dependent on the boiling point of the solvent used. However, the temperature may not be higher than about 100° C. in order to keep the oxygen sufficiently in solution.

In the terms (1-7C)alkyl, (1-6C)alkoxy and (1-4C)alcohols the alkyl group is a branched or unbranched alkyl group having 1 to 7, 1 to 6 or 1 to 4 carbon atoms, respectively, such as methyl, ethyl, isopropyl, t-butyl, heptyl and the like.

The compound of formula III may suitably prepared by methods well known in the art. Preferably, the process for the preparation of a compound of formula III comprises reactively contacting a morphine derivative of formula II

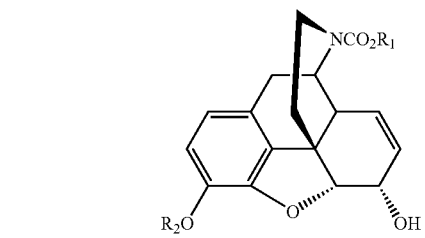

II with an oxidizing agent effective for oxidizing allylic hydroxy groups to form keto groups, where a morphinone compound of the formula III is prepared. Preferably, the oxidizing agent is sodium dichromate. Preferably $R_1$ is ethyl. For $R_2$ benzyl is most preferred.

The new process of this invention may conveniently be used in the production of noroxymorphone. Therefore, another aspect of this invention is a process for the production of noroxymorphone, comprising a reaction step wherein a morphinone compound of formula III is oxidized into the 14-hydroxynormorphinone derivative of formula IV. In particular preferred is the process further comprising the oxidation of a morphine derivative of formula II into the compound of formula III as described above.

Especially preferred is a process for the production of noroxymorphone comprising the steps:

(a) converting morphine having the formula I

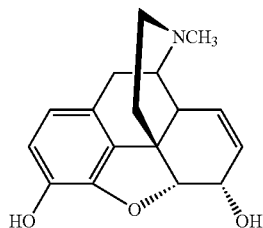
I by reaction with a haloformate ester of the formula X—C (=O)OR$_1$, wherein R$_1$ is as previously defined and X is a halogen (F, Cl, Br or I, preferably Cl), followed by a reaction with R$_2$—X, wherein X (preferably Cl) and R$_2$ are as previously defined, to form a morphine derivative of formula II;

(b) oxidizing the morphine of formula II to form a morphinone derivative of formula III according to the previously described process;

(c) oxidizing the morphinone derivative of formula III to form a 14-hydroxynormorphinone derivative of formula IV according to the previously described process;

(d) deprotecting the 3-position and (at the same time) reducing the double bond at the 7,8-position of the 14-hydroxynormorphinone derivative of formula IV to form a 3,14-hydroxynormorphinone derivative of formula V, using methods well known in the art for such type of reaction, e.g. using hydrogen and palladium-carbon as a catalyst,

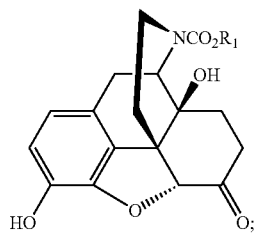
V (e) and hydrolyzing the 3,14-hydroxynormorphinone derivative of formula V into noroxymorphone of formula VI, using methods well known in the art for such type of hydrolysis, e.g. using sulfuric acid,

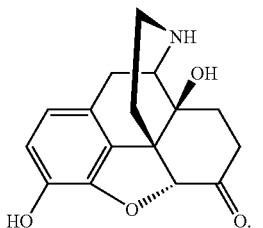
VI

In the process for the production of noroxymorphone, the novel intermediates of formula II, III and IV form each another aspect of the present invention. The intermediates of formula II, III and IV are in particular preferred wherein R$_1$ is ethyl. Also preferred are intermediates of formula II, III and IV wherein R$_2$ is benzyl. Most preferred are the intermediates of formula II, III and IV wherein R$_1$ is ethyl and R$_2$ is benzyl.

The invention is further illustrated by the following example.

EXAMPLE 1

The underlined numbers refer to the numbers of the structures of Scheme I. (Bn=benzyl).

(5α, 6α)-3-(benzyloxy)-7,8-didehydro-4,5-epoxy-6-hydroxymorphinan-17-carboxylic acid ethylester (2)

Morphine (1, 8 g) was dissolved in 80 ml of toluene and the solution was dried by azeotropic distillation of water. Sodium carbonate (15 g) and sodium hydrogen carbonate (6 g) were added and the solution was again dried by azeotropic distillation. Ethyl chloroformate (30 g) was slowly and in portions added over a period of approximately 4 h at 78° C. Completion of the reaction was checked with TLC. The excess of reagent and the salts were dissolved by addition of water. The layers were separated and the toluene layer was washed with water. The toluene solution was evaporated to dryness and the residue was dissolved in 70 ml of ethanol. The 3-carboxylic acid ethyl ester group was saponified by 6 g potassium hydroxide (dissolved in 18 ml of ethanol) and 5 g potassium carbonate at 55° C. The pH was checked (in a 1:1 dilution in water) and was >11. To this basic solution 5 g benzylchloride was added and the reaction was performed for 4 h at 75° C. The product was precipitated by the addition of water (70 ml), filtered, washed with water and dried. The yield of product (2) was 10 g. $^1$H NMR (600 M, CDCl$_3$) δ 1.29 (m, 3H), 1.92 (m, 2H), 2.52 (s, 1H), 2.72 (m, 2H), 2.85 (m, 1H), 3.01 (m, 1H), 4.01 (m, 1H), 4.17 (m, 3H), 4.87 (d, 1H), 4.89 (d, 1H), 5.09 (d, 1H), 5.18 (d, 1H), 5.29 (t, 1H), 5.72 (t, 1H), 6.53 (d, 1H), 6.75 (d, 1H), 7.37 (m, 5H).

(5α)-3-(benzyloxy)-7,8-didehydro-4,5-epoxy-6-oxomorphinan-17-carboxylic acid ethylester (3)

A solution of Jones reagent was prepared by dissolving 7,5 g sodium dichromate.2H$_2$O in 22 ml water and 6 ml sulfuric acid. Compound (2) (7,5 g) was dissolved in 60 ml trichloro ethylene and 28 ml water was added. The pH was adjusted to 5 with sulfuric acid. The mixture was heated under reflux and the Jones reagens was slowly added over a period of 1 h. The oxidation was continued for another 1,5 h under reflux. The excess of oxidant was destroyed with 6 ml 2-propanol. The layers were separated and the organic layer was washed with 10% sodium hydrogen carbonate solution and water and dried with sodium sulfate. The solution was evaporated to dryness and the residue was dissolved in ethanol. Yield: ~9 g product (3). $^1$H NMR (200 MHz, CDCl$_3$) δ 1.28 (m, 3H), 1.92 (m, 2H), 2.8 (m, 2H), 2.9 (m, 1H), 4.02 (m, 1H), 4.19 (m, 2H), 4.72 (s, 1H), 5.03 (m, 1H), 5.18 (s, 2H), 6.12 (dd, 1H), 6.57 (d, 1H), 6.64 (in, 1H), 6.74 (d, 1H), 7.34 (m, 5H).

(5α-3-(benzyloxy)-7,8-didehydro-4,5-epoxy-14-hydroxy-6-oxomorphinan-17-carboxylic acid ethylester (4)

The solution of product (3) in ethanol (9 g in 135 ml) was heated to 60° C., 2,6 g cobalt (II) acetate and 0,5 g sodium acetate were added and air was bubbled through the solution under vigorous stirring. The reaction was followed with TLC. After completion of the reaction the solution was treated with charcoal (0,3 g) and filtered. The solution was distilled to volume and this concentrated solution (6,3 g (4) in 53 ml of ethanol) was transferred to the next step. $^1$H NMR of 4 (360

MHz, CH₃OH-d4) δ 1.28 (m, 3H), 1.55 (m, 1H), 2.52 (m, 1H), 2.74 (m, 1H), 2.92 (m, 2H), 4.05 (m, 1H), 4.15 (m, 2H), 4.64 (m, 1H), 4.72 (s, 1H), 4.85 (m, 1H), 5.1 (s, 2H), 6.05 (d, 1H), 6.6 (d, 1H), 6.76 (d, 1H), 6.91 (m, 1H), 7.3 (m, 5H).

(5α)-4,5-epoxy-3,14-dihydroxy-6-oxomorphinan-17-carboxylic acid ethylester (5)

To the solution of the previous step 6 ml of acetic acid was added. The product (4) was reduced with hydrogen and palladium-carbon (5%) as a catalyst (0,9 g) at 20° C. and normal pressure. After filtration and evaporation of ethanol 5,4 g of crude product (5) was obtained. The product was recrystallized from 2 parts (w/v) of ethyl acetate to obtain 4,7 g product (5).

(5α)-4,5-epoxy-3,14-dihydroxymorphinan-6-one (noroxymorphone) (6)

Product (5) (4,7 g) was dissolved in 28 ml of water and 5,6 ml of sulfuric acid and refluxed for approx. 24 h. The product was precipitated at pH=9 by dilution with water and 4,6 g of crude product (6) was obtained after filtration and drying. The product was purified by dissolution in ethanol, precipitation from this solvent at pH=2, dissolution in water, charcoal treatment and precipitation at pH=9. ¹H NMR (400 M z, DMSO-d6) δ 1.17 (m, 1H), 1.41 (m, 1H), 1.72 (m, 1H), 2.07 (m, 1H), 2.29 (m, 1H), 2.36 (m, 1H), 2.62 (in 1H), 3.9 (m, 4H), 6.52 (d, 1H), 6.56 (d, 1H).

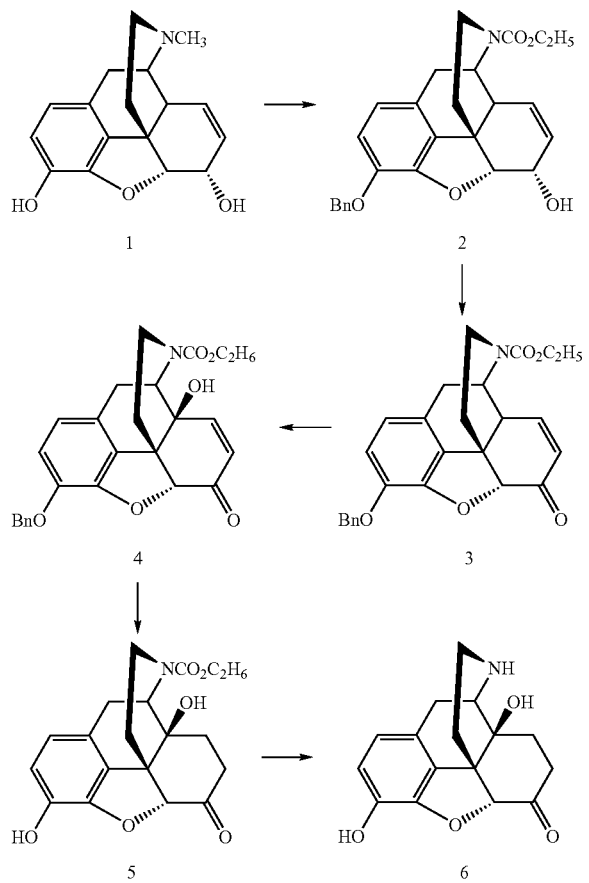

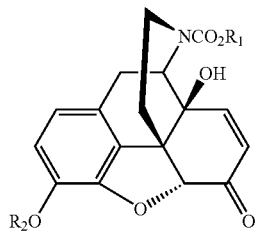

comprising reacting the compound of formula III,

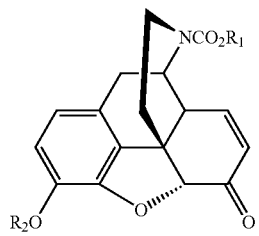

with a cobalt (II) oxidant in the presence of a mild base and air or oxygen as the cooxidant;
wherein
$R_1$ is (1C-7C)alkyl optionally substituted with one or more chlorines, butenyl, vinyl, benzyl, phenyl or naphthyl; and
$R_2$ is benzyl or benzyl substituted with one or more (1C-6C)alkoxy group or benzyl substituted with one or more halogen.

2. The process of claim 1, wherein the oxidant is Co(OAc)₂.

3. The process of claim 1, wherein the cooxidant is oxygen.

4. The process of claim 1, wherein the mild base is sodium acetate, potassium acetate, sodium phosphate or potassium phosphate.

5. The process of claim 4, wherein the mild base is sodium acetate.

6. The process of claim 1, wherein $R_1$ is (1-7C)alkyl.

7. The process of claim 6, wherein $R_1$ is ethyl.

8. The process of claim 1, wherein $R_2$ is benzyl.

9. A 14-hydroxynormorphinone compound of the formula IV

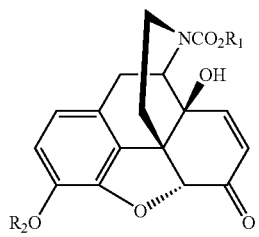

wherein
$R_1$ is (1C-7C)alkyl optionally substituted with one or more chlorines, butenyl, vinyl, benzyl, phenyl or naphthyl; and

What is claimed is:

1. A process for the preparation of a 14-hydroxynormorphinone compound of formula IV $R_2$ is benzyl or benzyl substituted with one or more (1C-6C)alkoxy group or benzyl substituted with one or more halogen.

10. The 14-hydroxynormorphinone compound of claim 9, wherein $R_1$ is ethyl.

11. The 14-hydroxynormorphinone compound of claim 9, wherein $R_2$ is benzyl.

12. A morphinone compound of the formula III

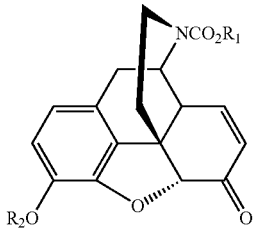

wherein
   $R_1$ is (1C-7C)alkyl optionally substituted with one or more chlorines, butenyl, vinyl, benzyl, phenyl or naphthyl; and
   $R_2$ is benzyl or benzyl substituted with one or more (1C-6C)alkoxy group or benzyl substituted with one or more halogen.

13. The morphinone compound of claim 12, wherein $R_1$ is ethyl.

14. The morphinone compound of claim 12, wherein $R_2$ is benzyl.

15. A process for the preparation of a compound of formula III

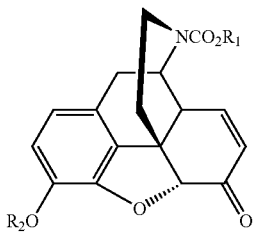

wherein
   $R_1$ is (1C-7C)alkyl optionally substituted with one or more chlorines, butenyl, vinyl, benzyl, phenyl or naphthyl; and
   $R_2$ is benzyl or benzyl substituted with one or more (1C-6C)alkoxy group or benzyl substituted with one or more halogen,
comprising: reactively contacting a morphine compound of formula II

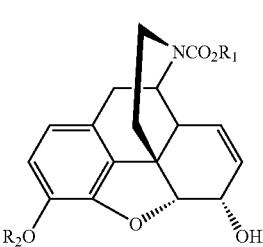

wherein $R_1$ and $R_2$ are as defined above, with an oxidizing agent effective for oxidizing allylic hydroxy groups to form keto groups, to form the compound of formula III.

16. The process of claim 15, wherein the oxidizing agent is sodium dichromate.

17. The process of claim 15, wherein $R_1$ is ethyl.

18. A process for the production of noroxymorphone, comprising: a reaction step wherein a morphinone compound of formula III

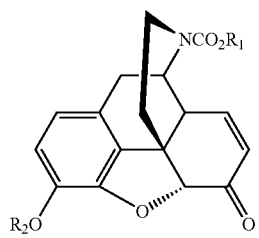

is oxidized into a 14-hydroxynormorphinone compound of formula IV

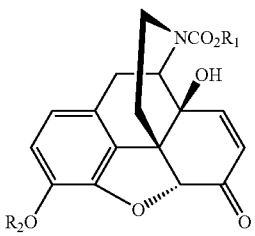

with a cobalt (II) oxidant in the presence of a mild base and air or oxygen as the cooxidant;
wherein
   $R_1$ is (1C-7C)alkyl optionally substituted with one or more chlorines, butenyl, vinyl, benzyl, phenyl or naphthyl; and
   $R_2$ is benzyl or benzyl substituted with one or more (1C-6C)alkoxy group or benzyl substituted with one or more halogen.

19. The process of claim 18, further comprising reactively contacting a compound of formula II

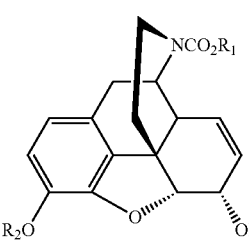

wherein $R_1$ is (1C-7C)alkyl optionally substituted with one or more chlorines, butenyl, vinyl, benzyl, phenyl or naphthyl; and
$R_2$ is benzyl or benzyl substituted with one or more (1C-6C) alkoxy group or benzyl substituted with one or more halogen, with an oxidizing agent effective for oxidizing allylic hydroxy groups to form keto groups, to form a morphinone compound of formula III wherein $R_1$ and $R_2$ are as defined above.

20. A process for the production of noroxymorphone, wherein morphine having the formula I

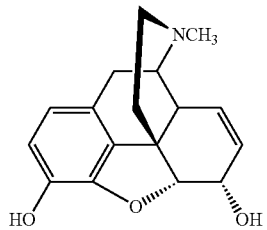

is converted into noroxymorphone, comprising:
(a) converting morphine having the formula I by reaction with a haloformate ester of the formula X—C(=O)OR$_1$, wherein $R_1$ is (1C-7C)alkyl optionally substituted with one or more chlorines, butenyl, vinyl, benzyl, phenyl or naphthyl and X is a halogen, followed by a reaction with $R_2$—X, wherein X is as previously defined and $R_2$ is benzyl or benzyl substituted with one or more (1C-6C)alkoxy group or benzyl substituted with one or more halogen, to form a morphine compound of formula II

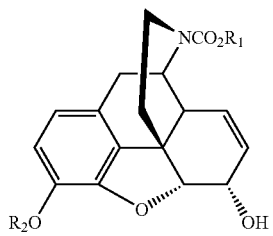

wherein $R_1$ and $R_2$ are as defined above,
(b) oxidizing the morphine of formula II to form a morphinone compound of formula III
wherein R1 and R2 are as defined above,
wherein the process is reactively contacting a morphine compound of formula II with an oxidizing agent effective for oxidizing allylic hydroxy groups to form keto groups;
(c) oxidizing the morphinone compound of formula III with a cobalt (II) oxidant in the presence of a mild base and air or oxygen as the cooxidant to form a 14-hydroxynormorphinone compound of formula IV
wherein $R_1$ and $R_2$ are as defined above;
(d) deprotecting the 3-position and reducing the double bond at the 7,8-position of the 14-hydroxynormorphinone compound of formula IV to form a 3,14-hydroxynormorphinone compound of formula V,

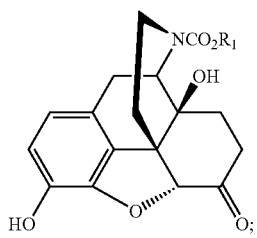

wherein $R_1$ is as defined above;
(e) and hydrolyzing the 3,14-hydroxynormorphinone compound of formula V into noroxymorphone of formula VI,

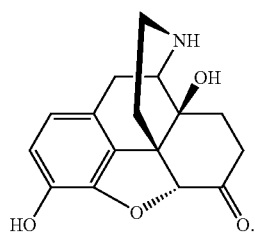

21. The process of claim 1, wherein the cooxidant is air.
22. The process of claim 15, wherein $R_2$ is benzyl.

* * * * *

UNITED STATES PATENT AND TRADEMARK OFFICE
CERTIFICATE OF CORRECTION

PATENT NO.         : 7,435,817 B2
APPLICATION NO.    : 10/487884
DATED              : October 14, 2008
INVENTOR(S)        : Linders et al.

It is certified that error appears in the above-identified patent and that said Letters Patent is hereby corrected as shown below:

On the Title page,

[*] Notice:   Subject to any disclaimer, the term of this patent is extended or adjusted under 35 USC 154(b) by 306 days Delete the phrase "by 306 days" and insert -- by 435 days --

Signed and Sealed this

Third Day of November, 2009

David J. Kappos
*Director of the United States Patent and Trademark Office*